United States Patent [19]

Jacobs

[11] 4,397,641
[45] Aug. 9, 1983

[54] CATHETER SUPPORT DEVICE

[76] Inventor: Daimon C. Jacobs, 9493 E. 139th St., Bixby, Okla. 74008

[21] Appl. No.: 250,534

[22] Filed: Apr. 3, 1981

[51] Int. Cl.³ ............................................. A61M 25/02
[52] U.S. Cl. .............................. 604/180; 128/DIG. 26
[58] Field of Search ............... 128/214 R, 348–350 R, 128/DIG. 26, 133; 604/180

[56] References Cited

U.S. PATENT DOCUMENTS

| | | | |
|---|---|---|---|
| 2,018,322 | 10/1935 | Saually | 128/350 R |
| 3,138,158 | 6/1964 | Gordon et al. | 128/DIG. 26 |
| 3,288,137 | 11/1966 | Lund | 128/133 |
| 3,568,679 | 3/1971 | Reif | 128/349 |
| 3,900,026 | 8/1975 | Wagner | 128/133 |
| 3,937,224 | 2/1976 | Vecker | 128/348 |
| 3,942,528 | 3/1976 | Loeser | 128/214 R |
| 4,040,427 | 8/1977 | Winnie | 128/348 |
| 4,316,461 | 2/1982 | Marais et al. | 128/214 R |

Primary Examiner—Dalton L. Truluck
Attorney, Agent, or Firm—Head, Johnson & Stevenson

[57] ABSTRACT

A catheter support device for anchoring an intravenous catheter and a portion of its associated tubing to a patient including a substantially rigid annular support member securable to the patient by an adhesive patch, the support member having an inclined catheter bracket mounted thereon for immobilizing the catheter with respect to the patient and an arcuate passageway carried by the support member for mechanically isolating a portion of the catheter tubing with respect to the catheter.

4 Claims, 4 Drawing Figures

CATHETER SUPPORT DEVICE

BACKGOUND OF THE INVENTION

1. Field of the Invention

The present invention relates to a catheter support device and more particularly, but not by way of limitation, to a catheter patch for carrying both the catheter and a portion of its associated tubing in a manner to reduce physical trauma to the patient and provide for more efficient maintenance of an aseptic area around the catheter.

2. History of the Prior Art

Intravenous infusion and removal of fluid from a person's body utilizing a catheter has been widely practiced for many years. However, the present methods used often result in the patient experiencing unnecessary discomfort and also physical harm both from trauma and infection.

The presently accepted methods include clipping or shaving the patient's hair in the area of the intended puncture, cleaning the site and inserting the needle-bearing catheter. The needle is then retracted and the catheter is taped to the patient's skin. The flexible tubing associated with the catheter is then looped and likewise taped to the patient's skin to prevent dislodging of the tube or the catheter.

This system has several disadvantages. First, shaving or clipping the hair about the site can result in razor cuts or nicks, which can give rise to infection. Further, extreme care must be taken to insure that the clippings are completely removed lest they contaminate the site.

The needle-bearing catheter, by necessity, must be inserted at an elevated angle with respect to the patient's skin surface. Hence, taping the catheter down against the skin causes a pivotal action at the puncture site, which can cause the catheter to tear a vein or to otherwise cause physical trauma to the patient.

Further, periodic removal of the tape to check the puncture site is both painful to the patient and exposes the site to contamination. The typical loop formed in the tubing associated with the catheter can become compressed, pinched or damaged by movement of the patient during long intravenous infusions.

Several attempts have been made to overcome the above disadvantages, such as taught in the patent to Lund, U.S. Pat. No. 3,288,137, issued Nov. 29, 1966 for an "Anchoring Device", which amounts to a pedestal mounted bracket for supporting a catheter hub at a desired angle with respect to the patient's skin. However, the Lund device not only provides no provisions for maintaining an aseptic area around the site, but would actually aggravate attempts to prevent contamination of the site.

Another such device is taught in the patent to Wagner, U.S. Pat. No. 3,900,026, issued Aug. 19, 1975 for a "Device for Holding and Protecting Intravenous Injection Needles". The Wagner device again provides for maintaining the catheter hub at a pre-determined angle while attempting to protect the site from contamination. However, the back portion of the support device is open which would require additional stuffing or taping in order to prevent contamination of the site. Therefore, it is submitted that the state of the art at the present time is lacking in efficiency, protection and comfort to the patient.

SUMMARY OF THE PRESENT INVENTION

The present invention provides a catheter supporting device which is particularly designed and constructed for overcoming the above disadvantages.

The present invention comprises an annular support member made of substantially rigid material having an inclined catheter support bracket secured thereto and in open communication with an aperture through the center of the support member.

The bottom surface of the support member can then be mounted to an adhesive patch having a concentric aperture therethrough which exposes only the puncture site where the needle-bearing catheter is to be inserted.

The annular support member is further provided with an arcuate passageway for carrying a portion of the tubing associated with the catheter frictionally therein for mechanically isolating the tubing with respect to the catheter so that accidental pulling or jerking of the tubing will not cause the tubing to break loose from the catheter and further, since the tubing is inserted in an arcuate passageway, prevents pinching off of the tubing thereby cutting off the intravenous fluid.

Since the annular support ring is elevated above the puncture site and completely surrounds the puncture site, a soft pad of gauze or other material may be placed over the site to prevent contamination. Inspection of the site is then easily accomplished by simply removing the gauze protection without causing any physical discomfort to the patient at the puncture site.

Further, the support member and associated adhesive patch is capable of being constructed of inexpensive plastic materials and sterilely packaged as a disposable unit further guarding against contamination.

DESCRIPTION OF THE DRAWINGS

Other and further advantageous features of the present invention will hereinafter more fully appear in connection with a detailed description of the drawings in which.

DESCRIPTION OF THE PREFERRED EMBODIMENT

Figure 2:
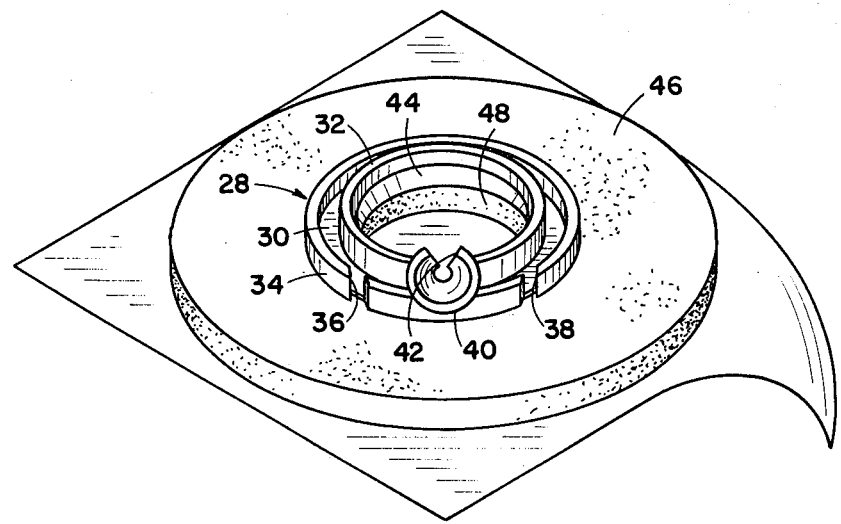
FIG. 2 is a perspective view of the support device of FIG. 1 with its protective backing.
Figure 1:
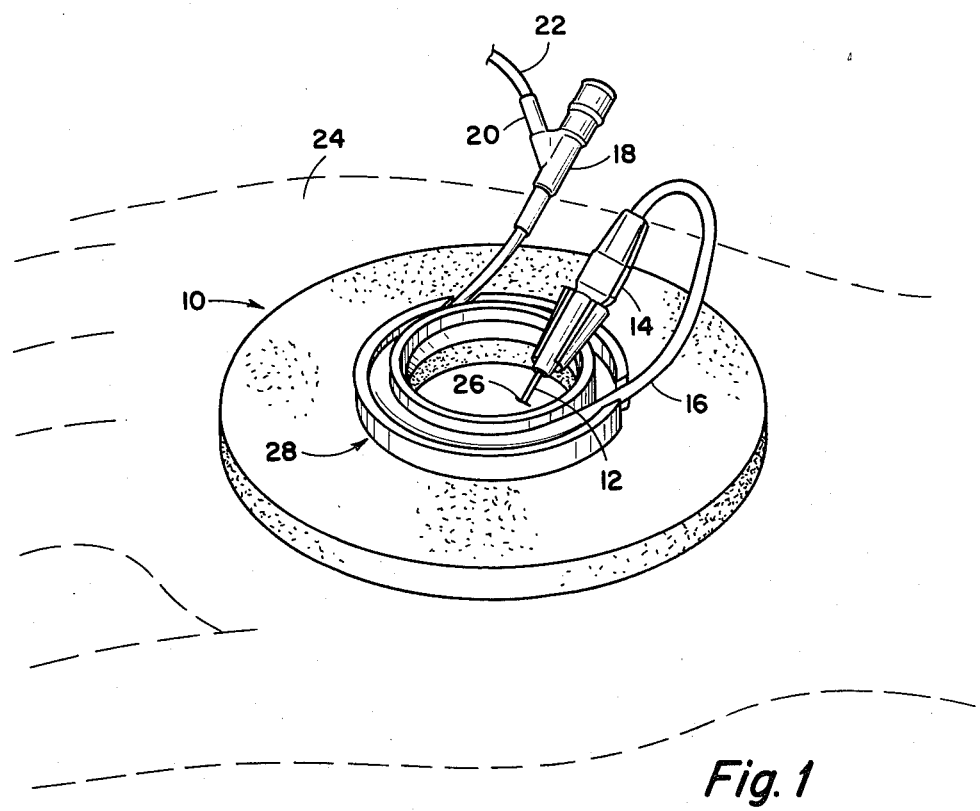
FIG. 1 is a perspective view of a catheter support device embodying the present invention with a catheter and associated tubing connected thereto.
Figure 3:
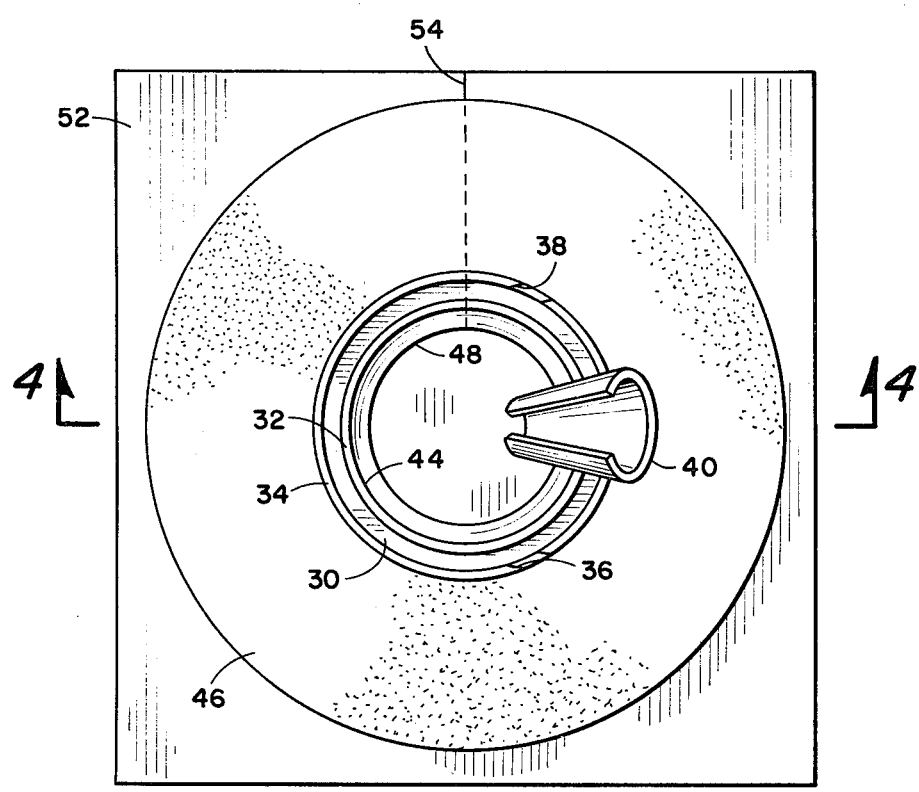
FIG. 3 is a plan view of the device of FIG. 2.
Figure 4:
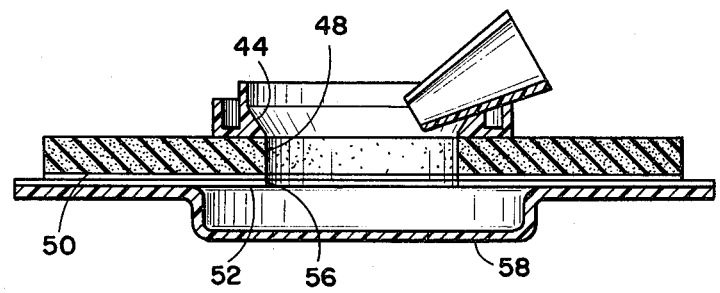
FIG. 4 is an elevational sectional view of the device of FIG. 3 taken along the broken lines 4—4 of FIG. 3.

Referring to the drawings in detail, reference character 10 generally indicates a catheter support device for anchoring an intravenous catheter indicated by reference character 12 along with its associated body or hub assembly 14 and connecting tubing 16. Typically, the tubing 16 may have attached a secondary or piggyback port assembly 18 and its primary infusion port 20 along with tubing 22 which may be connected to a fluid supply (not shown) for infusions or may be connected to a gathering container (not shown) when fluid is being withdrawn from a patient. The support 10 is shown attached to a patient's skin indicated by reference character 24 with the puncture site indicated by reference character 26.

The catheter support device 10 comprises an annular support member generally indicated by reference character 28 which is made of a substantially rigid material such as plastic. The support member comprises an annular base plate 30 having a pair of spaced concentric inner and outer wall members 32 and 34 secured to the top of the base 30 or made as an integral part thereof. The outer wall 34 is provided with a pair of substantially tangent spaced outlet apertures 36 and 38 for a purpose that will be hereinafter set forth.

A catheter support bracket 40 is secured to the upper edges of the inner and outer wall members 32 and 34. The support member is of a substantially truncated conical shape having an open top 42 and being set on an incline so that the smaller open end thereof is in open communication with an aperture 44 which is defined by the inner wall member 32.

A circular adhesive pad member 46 typically made of foam rubber is secured to the lower surface of the plate member 30 and is provided with an aperture 48 which is concentric with the aperture 44 and is also in communication with the lower end of the catheter bracket 40. The patch or pad member 46 is provided with a layer of diaphoretic resistant adhesive along the lower surface 50 thereof.

A first flexible cover member 52 is secured to the adhesive surface 50 of the pad member and is provided with a radial slit 54 from the outer edge to a central open aperture 56 which is concentric with the apertures 44 and 48. A second substantially rigid protective cover 58 may be secured to the bottom of the protection member 52 for maintaining the rigidity of the unit in its package (not shown).

In use, when the support device is removed from its package, the rigid protective cover 58 may be removed and discarded. The needle (not shown) carrying the catheter 12 may be passed through the aligned apertures in the support member 10 and inserted into the patient at a puncture site 26 after the area around the puncture site has been cleaned with a suitable antiseptic. After proper insertion has been made, the protective cover 52 may be torn away from the bottom of the adhesive patch 46 by means of the perforated line or slit 54.

The patch 46 then is secured to the patient's skin surface, the needle is removed from the catheter and the catheter hub 14 is attached to the catheter and placed in the bracket 40. The tube portion 16 associated with the catheter hub is then passed through the aperture 36 and pressed into frictional engagement with the passageway between the arcuate walls 32 and 34 with the opposite end of the tube portion 16 exiting the aperture 38. This tube may then be connected with a secondary or piggy-back port assembly 18 and connected to the primary tubing 22.

It is seen that the attachment of the support device to the patient's skin with the catheter hub being firmly carried by the bracket 40 immobilizes the said catheter with respect to the patient. The foam rubber patch 46 serves as a cushion to protect the patient's tissue at the puncture site.

The frictional carrying of the associated catheter tubing 16 within the passageway formed by the wall members 32 and 34 serves to mechanically isolate the catheter from the primary tubing 22 and the secondary port assembly 18 when in use.

The entire area over the puncture site 26 may be protected by gauze and tape as needed in order to maintain the puncture site free of contamination.

In order to periodically check the puncture site, the gauze and tape (not shown) may be removed leaving the puncture site relatively free of contamination for inspection. Since there is no tape in contact with the patient around the puncture site, little discomfort is experienced by the patient in periodically checking the intravenous connection.

From the foregoing it is apparent the present invention provides a simple disposable catheter support device which is both easy to manufacture and simple and efficient in operation.

Whereas the present invention has been described in particular relation to the drawings attached hereto, other and further modifications may be made within the spirit and scope of the invention. For example, the device as shown and described may be provided in a variety of sizes and may also be employed with other types of catheter uses such as intraarterial pressure lines and subclavian catheters.

I claim:

1. A catheter support device for anchoring a catheter and a portion of its associated tubing to a patient and comprising
a substantially rigid support member having inner and outer surfaces and an aperture therethrough for surrounding only the portion of the patient wherein the catheter is to be inserted, means carried by said support member inner surface for attaching said support member to the patient, a catheter bracket carried by the outer surface of the support member and being in open communication with the aperture therethrough for immobilizing the catheter with respect to the patient, an annular passageway provided in the outer surface of the support member surrounding the aperture for frictionally receiving a portion of the catheter associated tubing therein for substantially isolating said tubing portion with respect to the catheter, said support member comprising inner and outer circular spaced concentric outwardly extending wall members, the space therebetween being open between said wall members and forming said annular passageway, said catheter bracket being secured to said wall members, and wherein the outer wall member is provided with a pair of spaced openings therein to permit entry and exit of said portion of the catheter associated tubing.

2. A catheter support device as set forth in claim 1 and including an annular plate member secured to said wall members forming a base for said passageway, said plate member and wall members being secured to the means for attaching said support member to the patient.

3. A catheter support device as set forth in claim 1 wherein the means for attaching the support member comprises a flexible patch member having adhesive on one side thereof and an aperture therethrough concentric with the aperture in said support member, the flexible patch member being of a foam rubber material and including a peel-off cover member secured to the adhesive to protect said adhesive, and including a substantially rigid protective cover movably secured to the outer surface of the peel-off cover member for providing rigidity of said support device during shipment.

4. A catheter support device as set forth in claim 1 wherein said catheter bracket comprises a truncated conical shaped member having one side attached to the support member, the opposite side being provided with a longitudinal opening for receiving and holding the catheter therein.

* * * * *